United States Patent [19]

Spohr

[11] Patent Number: 4,778,657

[45] Date of Patent: Oct. 18, 1988

[54] APPARATUS FOR DETERMINING THE CHARACTERISTICS OF PARTICLES SUSPENDED IN LIQUIDS

[75] Inventor: Reimar Spohr, Darmstadt, Fed. Rep. of Germany

[73] Assignee: Kernforschungszentrum Karlsruhe GmbH, Karlsruhe, Fed. Rep. of Germany

[21] Appl. No.: 905,200

[22] Filed: Sep. 9, 1986

[30] Foreign Application Priority Data

Sep. 10, 1985 [DE] Fed. Rep. of Germany ....... 3532215

[51] Int. Cl.⁴ .......................................... G06M 11/04
[52] U.S. Cl. .................................... 422/73; 324/71.4; 377/11
[58] Field of Search ......................... 422/73; 324/71.4; 377/11

[56] References Cited

U.S. PATENT DOCUMENTS

| | | | |
|---|---|---|---|
| 3,628,140 | 12/1971 | Hogg et al. | 138/44 X |
| 3,739,180 | 6/1973 | Carlson | 377/11 |
| 3,845,386 | 10/1974 | Davies et al. | 377/11 |
| 3,890,568 | 6/1975 | Coulter et al. | 377/11 |
| 4,110,043 | 8/1978 | Eisest | 377/11 |
| 4,420,720 | 12/1983 | Newton et al. | 377/11 X |
| 4,438,390 | 3/1984 | Hogg | 377/11 X |
| 4,525,666 | 6/1985 | Groves | 324/71.4 X |

Primary Examiner—Barry S. Richman
Assistant Examiner—Jill Johnston
Attorney, Agent, or Firm—Spencer & Frank

[57] ABSTRACT

An apparatus for determining various characteristics of particles suspended in a liquid, e.g., the deformability or other values of red blood corpuscles. The particles are transported by a method similar to the Coulter method through a measuring channel having sections which are constricted or widened over the length of the measuring channel in, e.g., a foil. The change of certain electrical characteristics of the liquid is measured during passage of each particle, which furnishes a measure of the desired particle characteristics. The volume, as well as the deformability and other characteristics, of a particle can be determined during one passage through one and the same measuring channel. This is accomplished by forming a measuring channel composed of alternate constricted and widened portions in a step-like configuration which are a plurality of cylindrical channel sections, throughout the length of the channel. The cross-sections of the widened portions are larger than the cross-section of the particles to be examined, while the cross-section of the narrowed portions are smaller than the cross-sections of the particles.

16 Claims, 1 Drawing Sheet

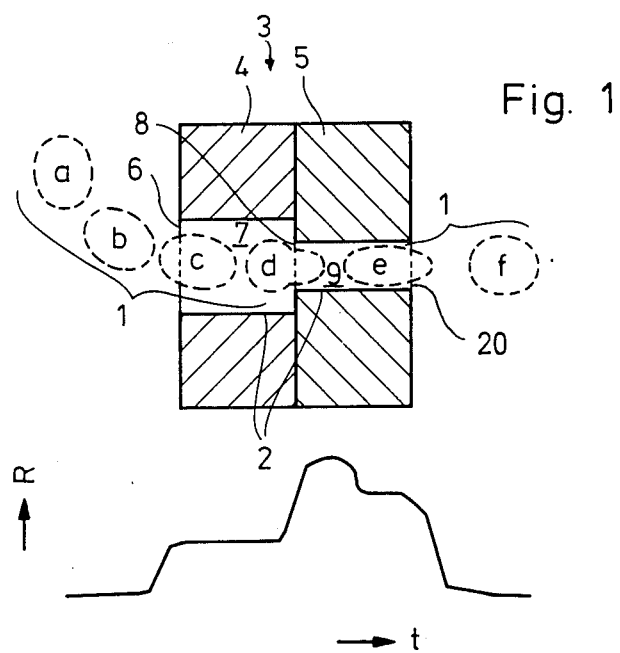
Fig. 1
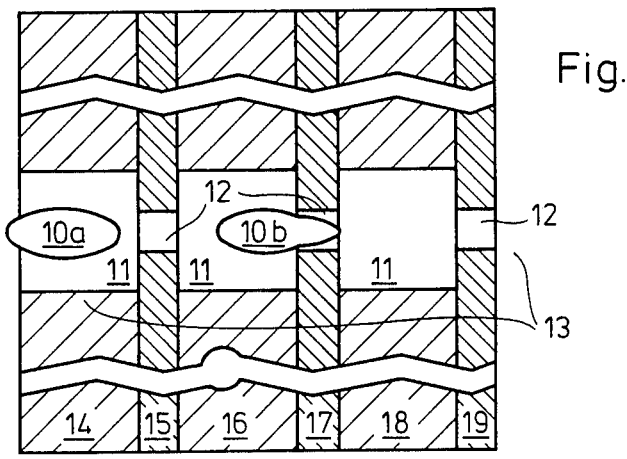
Fig. 2
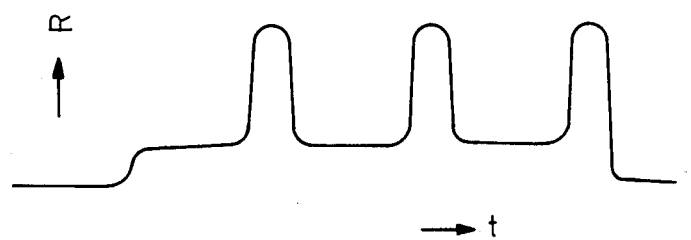

APPARATUS FOR DETERMINING THE CHARACTERISTICS OF PARTICLES SUSPENDED IN LIQUIDS

BACKGROUND OF THE INVENTION

1. Field of the Invention

The present invention relates to an apparatus for determining the characteristics of particles suspended in a liquid.

2. Description of the Related Art

The Coulter method is known, inter alia, for determining the number, size distribution and electrokinetic mobility of particles suspended in a liquid. This method was described in DE-AS 2,053,825. A conductance measuring cell in the form of a fine single pore or a capillary is used therein for this purpose. The diameter of such a cell or capillary is always larger than the particle, and its cross-section is uniform over its length. The funnel-shaped inlet zones connected upstream and downstream from the cell have an even larger cross-section and serve to preliminarily position the particles at the center of the pore. The particles are transported through the measuring pore by the flowing liquid or by means of an electric voltage drop. The change in resistance in the liquid during the passage of the particles through the measuring pore furnishes a measure of the particle volume or its mobility. The measuring capillaries in the Coulter apparatus have a diameter of about 70–100 microns. Moreover, the deformability of red blood corpuscles is quantized from a measurement of their passage through an unstructured channel of the same diameter or, more precisely, the same cross-section, as the channel having a smaller cross-section than the cross-section of the blood corpuscles.

The prior art methods for measuring either the number, volume, electrokinetic mobility or deformability of particles, all employ a cylindrical channel having a constant cross-section as the actual measuring zone. With such type of uniformly configured capillary, the information provided by the measuring method is limited, however, to merely the deformability of the particle.

Accordingly, based on the described state of the art, there is still a need for a device in which volume, as well as deformability and other characteristics, may be determined in a single passage through one and the same measuring channel which can avoid the drawbacks of the prior art devices, such as avoidance of field distortion at the inlet and outlet resulting from improved impingement conditions at the actual measuring pore, avoidance of the occurrence of non-axial particle paths and avoidance of cyclically returning particles in larger pore cross-sections.

SUMMARY OF THE INVENTION

This invention provides an apparatus for determining the characteristics of particles suspended in a liquid, the improvement comprising a cylindrical channel-shaped aperture comprising a plurality of alternate stepwise constricted and widened portions through which the particles are transported, wherein the cross-section of the widened portions is larger than the cross-section of the particles and the cross-section of the constricted portions is smaller than the cross-section of the particles; and a plurality of means for measuring the characteristics of the particles placed at the widened and constricted portions, wherefrom average values of each of the characteristics thereof can be obtained.

Other objects, advantages and features of the present invention will become apparent to those skilled in the art from the following discussion.

Applicants have found that the present stage-like widened and narrowed configuration of a cylindrical measuring channel having a channel-shaped measuring aperture, e.g., in a foil, in the form of a plurality of stepped channel sections connected in series, permits the attainment of a succession of multiple deformations of one and the same particle, which had been impossible in the past with the prior art channels. By means of the repeated steps, the practical result is a repeated measurement of the characteristics of one and the same particle from which an average can be calculated. This average reflects much better the characteristics of the particle than a one-time measurement according to the prior art methods. The initial conditions at the deformability-measuring aperture and at every stage thereafter, are improved by the repeatedly renewed uniform alignment of the particle before it enters into the narrow parts. The present invention thus permits for the first time a "simultaneous" determination of volume, deformability and shape of one and the same particle in one measuring process or one passage. The number of particles can of course also be determined in this way.

A variety of liquids which are harmless to the particles can be used to form the suspension, as is known in the art. The apparatus can be used for measurements of the characteristics of a large group of particles, including live cells such as red blood cells, bacteria, and viruses, in an isotonic or isoosmotic solution, i.e., aqueous solution.

A major advantage of such a multiple channel sectioned structure lies in the following characteristic features.

Orientation of the particle:

In the wide channel sections, an elongated particle is axially oriented in the laminar flow of the liquid. Therefore, it arrives at the critical measuring opening in a well oriented state.

Measurement of the volume of the particle:

In the wide channel sections, the volume of the particle can additionally be measured easily from the increase in resistance of the liquid.

Measurement of the deformability of the particle:

In the narrow channel sections, the deformability of the particle can be measured.

Increased measuring accuracy:

The measurement of the volume, as well as the measurement of the deformability, are taken several times in succession for one and the same particle, corresponding to the number of wide and narrow channel sections.

A more complete appreciation of the invention and many of the attendant advantages thereof will be readily perceived as the same becomes better understood by reference to the following description of the accompanying drawing.

BRIEF DESCRIPTION OF THE DRAWING

FIG. 1 depicts a simple, stepped, channel-shaped measuring channel as the basic structure for determining number, volume and deformability of the suspended particles.

FIG. 2 depicts a measuring channel in multiple stages.

A more complete appreciation of the invention and many of the attendant advantages thereof will be readily obtained as the invention becomes better understood by reference to the following detailed description when considered in connection with the accompanying drawings.

DESCRIPTION OF THE PREFERRED EMBODIMENTS

According to FIG. 1, a simple, basic device for the simultaneous determination of volume and deformability of a particle 1 (positions a to f) is composed of a stepped cylindrical and channel-shaped measuring channel 2 which penetrates a foil 3. The foil 3 is composed of a first layer 4 and a second layer 5 bonded together, resulting in a measuring channel 2 formed as a two-layer structure. By this bonding technique, two or more nuclear trace-recording materials having different chemical characteristics may be inseparably connected with one another, for example, by means of ultrasound or coextrusion, as a laminated foil.

The bond in the form of a matrix is then bombarded with individual heavy ions of a certain energy and etched until the aperture has a desired geometry. The etching rate of the bonded materials is selected according to the desired channel graduation. The chemical characteristics of the bonded materials with respect to the etching medium determine the diameter ratios of the channel stages. This is done in correspondence with the number of bonded nuclear trace-recording materials.

FIG. 1 shows two layers. As described hereinabove, the two-layer composite, or more precisely, foil 3 of FIG. 1 is formed by two layers 4 and 5. It is, however, also possible, as shown in FIG. 2, to use a plurality of superimposed and firmly bonded layers.

Shown schematically in the top portion of FIG. 1 are six positions (a through f) depicting the passage of a deformable particle 1 through inlet aperture 6 and outlet aperture 20. In the bottom portion of FIG. 1, is shown the time correspondence of the electrical resistance R throughout the channel 2, each time corresponding to the position of the particle. A particle 1 moves along the channel 2 as follows.

Phase a:

An arbitrarily oriented particle 1, e.g. a red corpuscle, is caught by suction at the entrance of the aperture 6.

Phase b:

The particle 1 orients itself in the gradient of the intake area.

Phase c:

The particle enters a measuring zone 7. Elastic vibrations of the particle are reduced by friction forces. The volume of the particle 1 results from the plateau value of the electrical resistance in the measuring zone 7.

Phase d:

The particle 1 impinges with the proper orientation on deformability aperture 8 and begins to be deformed. The time required to deform particle 1 to the critical diameter of measuring zone 9, more precisely, a capillary 9, furnishes a measure of the deformability of the particle 1.

Phase e:

The further curve of the resistance in the measuring zone or capillary 9 furnishes a measure of the shape of the deformed particle 1.

Phase f:

The particle leaves the measuring zone or capillary 9 with the proper orientation and resumes its original shape.

At the top of FIG. 2 is depicted a measuring channel 13 in multiple stages, i.e., a plurality of sections as shown in FIG. 1 which are connected in series. The bottom of FIG. 2 shows a time correlation of the electrical resistance curve for the electrolyte-filled channel or aperture.

In this manner, a channel-shaped measuring channel 13 results which has a plurality of wide and narrow sections, 11 and 12, respectively. The wide sections 11 have a larger cross-section or diameter than the particles 10 to be examined. The narrower sections 12 have a smaller cross-section than the particles 10. The particles 10 in phase 10a, are shown in a wider section 11; in phase 10b, they are shown as they enter a narrower section 12. The entrance process (phase 10b) into the narrower section or narrower stage 12 corresponds to the sequence shown in FIG. 1. Phase 10a of FIG. 2, thus, corresponds to the position of the particle 1c in FIG. 1. Thus, the entire measuring channel 13 is composed of a series of stepped constrictions and widened portions one behind the other, each having associated cylindrical channel sections 11 and 12. Several of these sections are provided so that the deformation processes (10a and 10b) of passaging of a particle occur several times in succession for one and the same particle. Therefore, measuring channel 13 furnishes various measured values in succession for one and the same particle. That is, during one passage, different values are obtained for one particle more precisely since each particle is measured several times, with a new classification of the particle taking place for each measurement.

As already mentioned, channel 13 is provided by means of a multiple layer bonding technique. For this purpose, an appropriate number of layers (14 to 19), or an even greater number of layers, are inseparably connected to one another, and then irradiated and etched. By coordinating or selecting the etching characteristics of the respective layers (14 to 19), the desired diameter ratios of the constrictions, narrow portions 12, and wide portions 11 can then be set as desired.

With the novel measuring channel shown by means of example in FIGS. 1 and 2, the starting conditions are improved, particularly since the particles are uniformly aligned and particle vibrations are suppressed before the particles enter the critical measuring aperture. For this purpose, microscopically fine rotary bodies of any desired shape are used as the measuring pore. Due to the complex configuration of the measuring aperture as a stepped channel, various pieces of data are obtained from the passage of one particle through the measuring pore. For example, an individual characteristic signature for each particle can be obtained from the resistance curve during passage of the particle through the stages of the measuring channel even without quantitative analysis of the measured signal. As such, a type of "fingerprint" can be obtained for each particle. A novelty of the present invention resides in the simultaneous detection of a plurality of particle parameters in one and the same measuring process. This is attained by quantitative analysis of the resistance curve obtained during the passage of the particle through the measuring channel. In particular, the simultaneous measurement of volume and deformability of one and the same particle is possible during a single passage of that particle. Before each constriction in the measuring channel, the particle is again aligned properly. Accordingly, the above-described improvement of the starting conditions takes place again and again in the measuring channel.

Exemplary numerical values for cross-sectional dimension: large channel section 10–100 μm, small channel section ≦10 μm, length of each section ≧ twice of cross-section, number of sections 2–10, and variation range of dimension values approximately 10%.

As an example of the measuring process, red blood cells are suspended in an isotonic aqueous suspension and, according to FIGS. 1 and 2, arrive from the left side of the measuring channel.

The red cells first enter a wide section of the channel where they orient themselves axially and their volume is measured by observing the corresponding increase of the electrical resistance in the wide-section. Then, the red cells, which are well oriented, impinge onto the narrow-section of the channel. Therefore, particle deformability is measured in a well defined state. Since particle diameter is larger than the narrow-section of the channel, they cannot pass through it unless their shape is changed to fit through this narrow-section channel. The corresponding deformation requires energy which is supplied by the flow. Accordingly, the passage time through the narrow section depends on the cells deformability.

The invention now being fully described, it will be apparent to one of ordinary skill in the art that many changes and modifications can be made thereto without departing from the spirit or scope of the invention as set forth herein.

What is claimed is:

1. Apparatus for determining characteristics of particles which are deformable, have a normal cross-sectional dimension, and are suspended in a liquid, comprising:

means defining a cylindrical measuring channel through which the particles are successively transported one by one by causing the liquid in which the particles are suspended to flow therethrough and which comprises a plurality of constricted portions and a plurality of widened portions, each of the plurality of constricted portions alternating stepwise with a respective one of the plurality of widened portions, each of the plurality of widened portions having a cross-sectional diameter which is larger than the normal cross-sectional dimension of each particle, and each of the plurality of constricted portions having a cross-sectional diameter which ranges up to 10 μm and which is smaller than the normal cross-sectional dimension of each particle so that each particle is caused to deform as it is transported through each of the plurality of constricted portions, wherein the cross-sectional diameter of each of the plurality of widened portions does not exceed the cross-sectional diameter of each of the plurality of constricted portions by more than 10 times; and at least one means for measuring characteristics of each particle at the plurality of widened portions and at the plurality of constricted portions, respectively, wherefrom average values of each of the characteristics of each particle can be obtained.

2. The apparatus of claim 1, wherein the particles are red blood cells.

3. The apparatus of claim 1, wherein the cylindrical measuring channel has a longitudinal center axis and wherein the plurality of constricted portions are aligned along the longitudinal center axis.

4. The apparatus according to claim 1, wherein the at least one means for measuring the characteristics of each particle is capable of simultaneously determining volume, deformability, and deformed shape of each particle.

5. The apparatus according to claim 1, wherein the cross-sectional diameter of each of the plurality of widened portions is effective to maintain the successive, one by one transportation of the particles through the cylindrical measuring channel.

6. The apparatus according to claim 1, wherein the means defining a cylindrical measuring channel consists of means defining an inlet aperture, a plurality of constricted portions, a plurality of widened portions, and means defining an outlet aperture.

7. The apparatus of claim 1, wherein the at least one means for measuring the characteristics of each particle is capable of determining at least one of volume, deformability and deformed shape of each particle.

8. The apparatus of claim 7, wherein the at least one means for measuring the characteristics of each particle includes means for determining the deformability of each particle placed at the plurality of constricted portions of the cylindrical measuring channel whereby an average deformability measurement is obtained for each particle.

9. The apparatus of claim 7, wherein the at least one means for measuring the characteristics of each particle includes means for measuring the volume of each particle placed at the plurality of widened portions of the cylindrical measuring channel whereby an average volume measurement is obtained for each particle.

10. The apparatus of claim 9, wherein the means for measuring the volume of each particle measures changes in the electrical resistance of the liquid.

11. Apparatus for simultaneously determining volume and deformability of particles which are deformable, have a normal cross-sectional dimension, and are suspended in a liquid, the apparatus comprising:

means defining a cylindrical measuring channel through which the particles are successively transported one by one and which comprises a plurality of constricted portions and a plurality of widened portions, each of the plurality of constricted portions alternating stepwise with a respective one of the plurality of widened portions, each of the plurality of widened portions having a cross-sectional diameter which is larger than the normal cross-sectional dimension of each particle, and each of the plurality of constricted portions having a cross-sectional diameter which ranges up to 10 μm and which is smaller than the normal cross-sectional dimension of each particle so that each particle is caused to deform as it is transported through each of the plurality of constricted portions, wherein the cross-sectional diameter of each of the plurality of widened portions does not exceed the cross-sectional diameter of each of the plurality of constricted portions by more than 10 times; and at least one means for measuring characteristics of each particle at the plurality of widened portions and at the plurality of constricted portions, respectively, wherefrom average values of the characteristics of each particle can be obtained, wherein the characteristics to be measured include volume and deformability of the particles, wherein one of the at least one means for measuring characteristics of each particle is positioned at the plurality of widened portions of the cylindrical measuring channel and measures the average volume of each particle by measuring the volume of each particle at each of the plurality of widened portions, respectively, and wherein another of the at least one means for measuring characteristics of each particle is placed at the plurality of constricted portions of the cylindrical measuring channel and measures the average deformability of each particle by measuring passage time of each particle at each of the plurality of constricted portions, respectively.

12. The apparatus according to claim 11, wherein the characteristics to be measured further include deformed shape of the particles, wherein each of the at least one means for measuring characteristics of each particle is a means for measuring changes in the electrical resistance of the liquid, and wherein a curve of the electrical resistance versus time as each particle is transported one by one through and deformed in each of the plurality of constricted portions furnishes a measure of the deformed shape of each particle whereby an average deformed shape measurement is obtained.

13. The apparatus according to claim 11, wherein the particles are red blood cells.

14. The apparatus according to claim 11, wherein the measuring channel has a longitudinal center axis and wherein the plurality of constricted portions are aligned along the longitudinal center axis.

15. The apparatus according to claim 11, wherein the cross-sectional diameter of each of the plurality of widened portions is effective to maintain the successive one by one transportation of the particles through the cylindrical measuring channel.

16. The apparatus according to claim 11, wherein the means defining a cylindrical measuring channel consists of means defining an inlet aperture, a plurality of constricted portions, a plurality of widened portions, and means defining an outlet aperture.

* * * * *